United States Patent [19]
Bishop

[11] Patent Number: 6,036,831
[45] Date of Patent: *Mar. 14, 2000

[54] AUTOMATIC PROTEIN AND/OR DNA ANALYSIS SYSTEM AND METHOD

[75] Inventor: Robert Bishop, Newton Center, Mass.

[73] Assignee: Academy of Applied Science, Concord, N.H.

[ * ] Notice: This patent is subject to a terminal disclaimer.

[21] Appl. No.: 09/151,224

[22] Filed: Sep. 10, 1998

Related U.S. Application Data

[62] Division of application No. 08/859,532, May 20, 1998, Pat. No. 5,865,975, which is a continuation of application No. 08/467,838, Jun. 6, 1995, abandoned.

[51] Int. Cl.[7] .......................... G01N 27/26; G01N 27/447
[52] U.S. Cl. .......................... 204/618; 204/466; 204/467; 204/616
[58] Field of Search ...................................... 204/456, 457, 204/458, 499, 461, 462, 463, 464, 465, 466, 467, 468, 469, 470, 606, 607, 608, 609, 610, 612, 613, 614, 615, 616, 617, 618, 619, 620, 621

[56] References Cited

U.S. PATENT DOCUMENTS

| | | | |
|---|---|---|---|
| 4,360,418 | 11/1982 | Golias | 204/608 |
| 4,578,169 | 3/1986 | Vicario et al. | 204/641 |
| 4,986,891 | 1/1991 | Sarrine et al. | 204/608 |
| 5,865,975 | 2/1999 | Bishop | 204/618 |

*Primary Examiner*—Jill Warden
*Assistant Examiner*—John S. Starsiak, Jr.
*Attorney, Agent, or Firm*—Rines and Rines

[57] ABSTRACT

A fully automated protein and/or DNA gene fragment analyzing machine and method are disclosed in which, in a simple machine structure, a plurality of electrophoresis calls each containing such fragments, are robotically, under computer programming, inserted into an electrophoresis housing and subjected to voltage for producing electrophoretic migration in one dimension (horizontally), and then preferably after robotic 90° rotating of the cells, are voltage migrated in an orthogonal direction to separate the fragments vertically, and then robotically presented to an optical image scanner for identifying the brightest fragments and classifying the same, with comparison with reference image fragment locations of normal or variant fragments, and for computer storing all relevant data.

12 Claims, 10 Drawing Sheets

AUTOMATIC PROTEIN AND/OR DNA ANALYSIS SYSTEM AND METHOD

This application is a division of U.S. application Ser. No. 08/859,532, filed May 20, 1998 now U.S. Pat. No. 5,865,975 which is a FWC of Ser. No. 08/467,838, filed Jun. 6, 1995, now abandoned.

The present invention relates to the analysis of proteins and DNA genomes and the like, more particularly concerned with techniques and systems or apparatus for examining gene or protein fragments to determine defects or mutations in the same and to do so automatically inaccordance with novel approaches of the invention.

BACKGROUND OF INVENTION

Various techniques and apparatus have been developed and used for protein and for DNA diagnostic testing, the latter, for example, to uncover gene patterns with mutational defects predictative or indicative of a disease or the susceptibility to the same—for example, many of the common polygenic diseases like heart disease, cancers, neurodegenerative diseases, cystic fibrosis, Rb (retinablastoma) and many others.

DNA diagnostic testing often involves successive heat-separating or denaturing of the DNA strand pairs in the presence of appropriate reaction primers to produce a purified and amplified quantity of the so-called gene exons to enable viewing and image analysis of the patterns—so called polymerase chain reaction (PCR) amplification of gene exons, followed by electrophoretic separation of the resulting fragments (preferably 2D—two dimensionally to provide separation on the basis of both size and basepair sequence pattern separation), and inspection and image analysis of the electorphoretic fragment separation pattern image to observe variations from normal separations and thereby detect mutational defects.

In protein analysis, also, electrophoretic separation has been employed.

Since the present invention is concerned with the total automation of such a testing process and thus the integration and improvement of the various technologies, steps, and apparatus there involved, it is first important to examine the background state of the art of these individual technologies, steps and apparatus components.

HISTORY AND BACKGROUND OF APPLICABLE TECHNOLOGIES

Applicable technologies exist in each of the following five areas:

2-D electrophoresis with a chemical gradient
1-D electrophoresis with a temperature gradient
1-D electrophoresis with fluorescent labels
fluorescent scanners
image analysis of two dimensional DNA patterns Current technology in each of these areas will now be discussed in the order presented above.

2-D Electrophoresis With Chemical Gradient

Two-dimensional denaturing gradient gel electrophoresis (2D-DGGE) was first introduced by Fischer and Lerman in 1979 (ref. 1 listed in references cited at end of this specification). Fragments were separated in the first axis of a polyacrylamide gel on the basis of size. The gel was then manually rotated 90 degrees and the electrophoresis process was repeated. The second axis contained a chemical gradient of denaturants (e.g. a mixture of urea and formamide), distributed linearly along the axis of the gel. As the DNA fragments, typically 100 to 1000 basepairs long, migrated through the gradient, migration stopped when the concentration of denaturants was sufficiently high to cause the DNA double helix to unfold. The specific spatial position or corresponding value of this gradient is referred to as the melting point. This melting process thereby sorted the fragments as a function of their basepair sequence. Lerman and co-workers were able to distinguish two DNA fragments, completely identical to one another with the exception of a mutation in one of the fragments by observing a spatial shift in the position of the mutated fragment. When the basepair sequence of each fragment is known, their melting point position can be simulated on the basis of the "Melting Theory" using a computer-encoded algorithm (ref. 2). In spite of its theoretical capability to show the presence of all possible mutations in a given DNA fragment, 2D-DGGE was not widely applied due to the complexity of the method and the lack of sophisticated instrumentation.

A machine to eliminate the need to rotate the gel 90 degrees was introduced by Ingeny B. V., Leiden, The Netherlands in 1993. (ref. 3 and ref. 15), pioneered by Dr. Jan Vijg. The instrument can process up to 10 gels, which are each sandwiched between two glass plates and positioned vertically. The machine contains four isolated wells containing ionic buffer solution, and embodying four wells isolated by tight fitting gaskets as shown in later described FIG. 4.

The right and left wells, which contact the right and left edges of the gel, respectively, are filled and activated to perform a size separation in the horizontal direction. These wells are then drained and the top and bottom wells are filled. The upper and lower edges of the gel insert into, and make contact with, these top and bottom wells. The top and bottom wells are then activated to perform the second electrophoresis operation which sorts the fragments by basepair sequence in the vertical direction. Once the second electrophoresis operation is complete, a lab technician manually removes the gaskets and separates the glass plates to access the gels. Gels are then soaked in a fluorescent stain such as ethidium bromide (which is carcinogenic). Staining is required to visualize the pattern of DNA fragments appearing as spots on the gel. Gels are approximately 1 millimeter thick, extremely fragile and are prone to being damaged. Care must be taken to remove and wash off excessive stain absorbed into the gel so that good contrast can be obtained between the stained fragments and the gel background.

Gels are then placed onto a UV light box such as the Molecular Biology model BT200310, which excites the fluorescent stain. Either a Polaroid photographic picture of the fluorescent image is taken and the picture is scanned into a computer or a tv camera is used to replace the photographic process. An alternative method is to use a fluorescent scanner such as the Fluorimager 575 by Molecular Dynamics to directly scan the gel image into the computer) eliminating the need for the UV light box. The computer serves as an interactive measurement tool and display to assist the operator. To use the computer program, lab technicians must manually identify and supply the computer with the location of multiple (10–20) fragments.

These fragments are then used as reference calibration points by the program. The program then compares the spot pattern to a stored reference image and indicates fragment locations that don't match up. The program however cannot distinguish the difference between an actual fragment and a process artifact or byproduct that lies at an expected spot location. Therefore both the calibration procedure and the final decision whether a gene mutation is present heretofore had to be performed manually.

To summarize, the entire process consisting of: generating a 2-D electrophoresis pattern, staining the gel, imaging the stained sample and analyzing the data for mutations, is extremely labor intensive.

1-D Electrophoresis With A Temperature Gradient

One-dimensional gradient controlled electrophoresis systems have been used to sort DNA fragments according to basepair sequence. A 1-D electrophoresis system using a chemical gradient is produced, for example, by Bio-Rad (ref. 4). Sorting by sequence can also be achieved by replacing the chemical gradient with a temperature gradient. Riesner (ref.5),and others (ref. 6 & 7), constructed 1-D temperature gradient electrophoresis systems. In each of these systems, the thermal gradient was created by sandwiching the gel between two temperature controlled metal plates. A linear gradient was generated by having two different temperature controlled fluids flowing through channels at opposite ends of each plate as illustrated in later-described FIG. 5. Incorporating a temperature gradient instead of a chemical gradient simplifies the gel preparation process by eliminating the labor required to create the chemical gradient in each gel. The instrument becomes more complex to construct, however, and the mechanism for generating the temperature gradient can only produce a linear gradient. It will be shown later that, in accordance with a preferred design of the present invention, a programmable non-linear gradient is more useful because it can be optimized for detection of a given mutation.

1-D Blectrophoresis With Fluorescent Labels

The two previously described electrophoresis systems both required that DNA fragments be manually stained after completion of the process, so that an optical image of the fragments could be created. Molecular Dynamics (Fluorimager model 575, ref. 8), Applied Biosystems (373 DNA sequencer, ref. 9), LabIntelligence model HPGE 1000 (ref. 10) and others, have been able to attach fluorescent labels to DNA fragments prior to performing a one-dimensional electrophoresis size separation. Attaching the labels prior to the electrophoresis process eliminates the need to stain the fragments manually and possibly damage the fragile gel after processing.

Fluorescent Scanners

Fluorescent scanners have been in use for many years to create images of many different types of products. Companies such as Orbot, for example, manufacture circuit board inspection systems that fluoresce the printed circuit board laminate to obtain good contrast between the conductors and the surrounding laminate. In the biological arena, companies such as Molecular Dynamics (ref. 8) and Applied Biosystems (ref. 9) produce laser scanners for DNA analysis. A confocal laser scanner for use in DNA sequencing is described in Laser Focus World June 1994 (ref.11). Ultraviolet light sources, instead of lasers, have also been incorporated to fluoresce materials. "Black lights", as they are frequently called, are used to illuminate posters that glow in the dark. A UV light box, e.g. Molecular Biology model BT200310, has also been used in laboratories to excite fluorescent stains such as ethidium bromide. The LabIntelligence model HPGE 1000 (ref. 10) Gel Electrophoresis System for producing and scanning one-dimensional gels uses an ultraviolet bulb to excite fluorescently labeled DNA and protein samples.

Image Analysis of Two Dimensional DNA Patterns

Currently, image processing programs only assist an operator in detecting mutations. For example, an image analysis system produced by Ingeny (ref. 12) requires an operator manually to identify 10–20 reference "spot markers" equally distributed over the gel. These spot markers are used to calibrate the software program and compensate for process variations in gel preparation. Markers can either be fragments from the gene to be analyzed which are known not to contain mutations, or reference fragments mixed in during the preparation process. The program then applies a form of triangular normalization to these reference points to align them with a stored set of points for the specific gene of interest. A normalized form of template matching is then used to compare the other fragments on the gel to a pre-stored set of known spot fragments for the specific gene. The pre-stored set contains the location and variance for all fragments of interest. To minimize false alarms due to smearing and artifacts in the image, the algorithm only "looks" at specific locations where fragments are expected. The algorithm, however, does not have any intelligence to distinguish the difference between a valid fragment and an artifact appearing at the spot location.

OBJECTS OF INVENTION

An object of the present invention, accordingly is to provide a new and improved method of and system and apparatus for the diagnostic testing of DNA fragments, proteins and similar items, that shall not be subject to any of the above described difficulties or limitations of prior techniques, apparatus or components, and that, to the contrary, provides for the fully automated gene, protein or similar analysis.

A further object is to provide improvements in each of electrophoretic apparatus, automatic handling of the same, and image scanning and computer analysis thereof, including novel algorithmic approaches to enable such a fully automatic diagnostic clinical system to be achieved.

Other and further objects will be explained hereinafter and are more particularly delineated in the appended claims.

SUMMARY

In summary, however, from one of its most important aspects, the invention embodies a method of automatically analyzing gene fragment samples that have been obtained in numerous copies through polymerase chain reaction amplification, that comprises, providing at a baseline location a plurality of optically transparent gel cells, each containing such a sample; robotically, under computer program control, sequentially transporting the successive cells to a corresponding position in an electrophoresis housing; applying voltage transversely of the housing to effect electrophoretic migration of the gene fragments horizontally in each gel cell, horizontally to separate the gene fragments by size; upon completion of such migration, under said program control, robotically sequentially lifting the successive cells from the housing, rotating them through 90°, and then placing them back in their said positions in the electrophoresis housing; establishing, under said program control, a predetermined temperature gradient across the cells; reapplying voltage transversely of the housing to effect electrophoretic migration of the gene fragments vertically to separate the fragments as a function of basepair sequence; robotically then sequentially presenting each cell for image optical scanning; during said scanning and under said program control, identifying and contrasting the brighter gene fragments and their locations while distinguishing the same from smears and other artifacts; automatically classifying the identified fragments and comparing the same with reference locations and spatial offsets of normal and of mutated genes; and robotically thereupon returning the scanned cells to said loading or other location while storing all pertinent data related to the scanned gene fragments in the computer.

The invention, indeed, provides what is believed to be the first fully automated system to detect human susceptibility to, and diagnosis of, gene and protein related disorders. As before explained, primary applications of the system include screening individuals for cancers (breast, colon, lung, etc.), hereditary diseases (cystic fibrosis, etc.) and detecting serum and urine protein irregularities among other applications, and including genetic fingerprinting as for such application as forensic analysis.

Scientists, as earlier stated, have determined that a defect in any one of several different genes can cause a specific type of cancer. For example, defects in any one of seven different genes can cause colon cancer. The system of the present invention is the first also to be able to analyze multiple genes from the same patient simultaneously, and concurrently analyze genes from multiple patients, as well.

The invention has been particularly developed for clinical applications in which ease of use and volume processing is extremely important. Operation consists of having a lab technician insert fluorescently labeled biological preparations into a loading station. The system, then, under automated robotic control, transports the preparations through various stages of biological processing. Once the biological phase is complete, the robot transports the samples to an internal image processing station for automated computer analysis of the complex images. The novel computer algorithms indicate whether mutations are present and in which individuals. After analysis, the robot arm returns the samples to the loading station for removal from the instrument.

Preferred and best mode techniques and apparatus designs and implementation will later be detailed.

DRAWINGS

The invention will now be described with reference to the accompanying drawings, FIG. 1 of which is an overall diagram of a preferred system machine for enabling fully automatic DNA, protein and similar diagnostic analysis in accordance with the invention;

Figure 1:
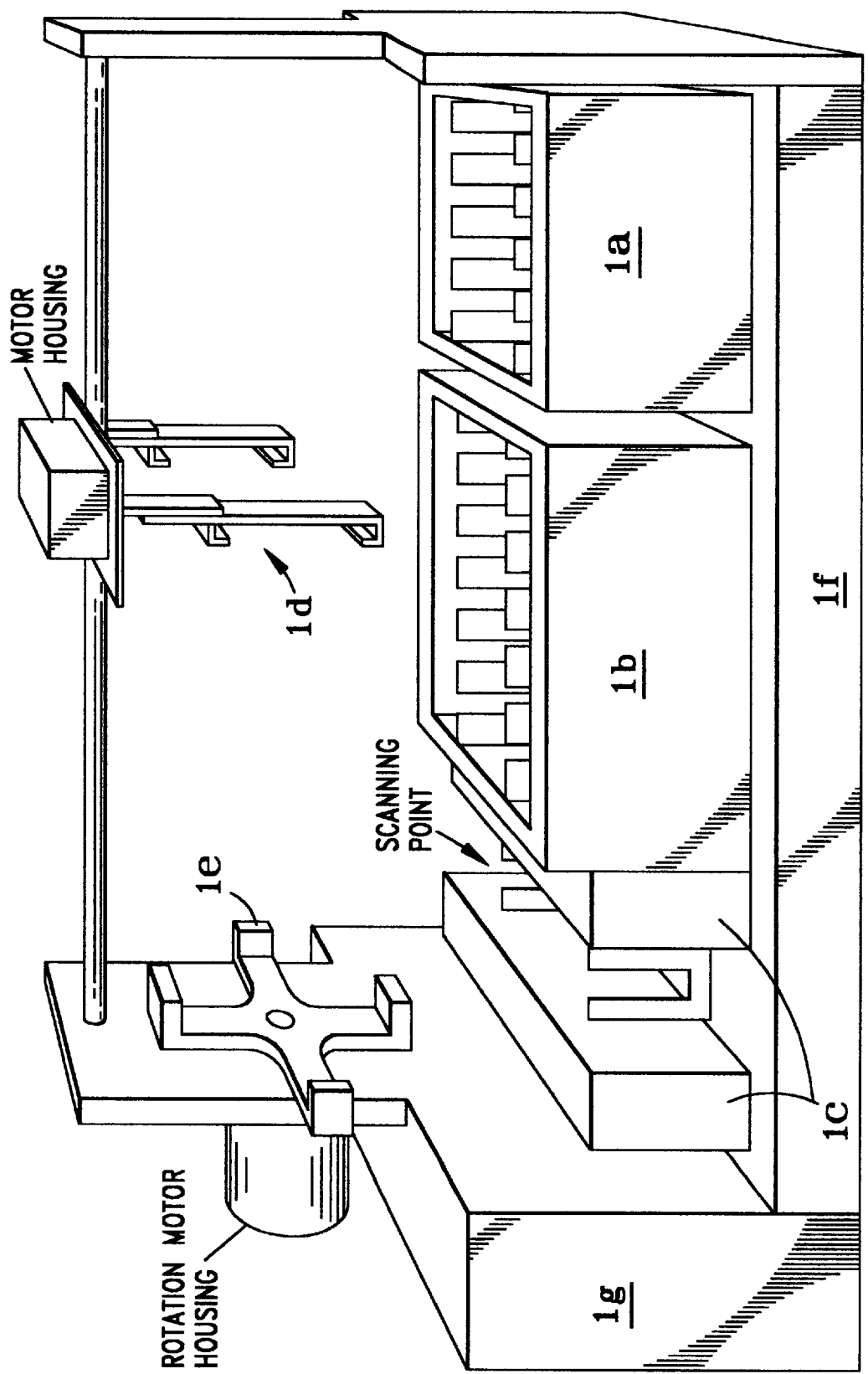
Figure 6A:
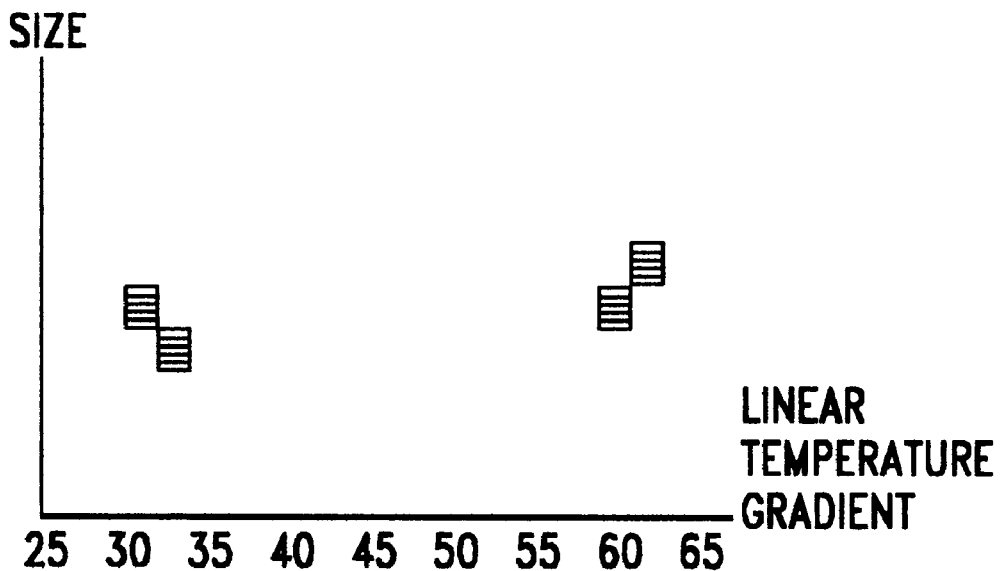
Figure 6B:
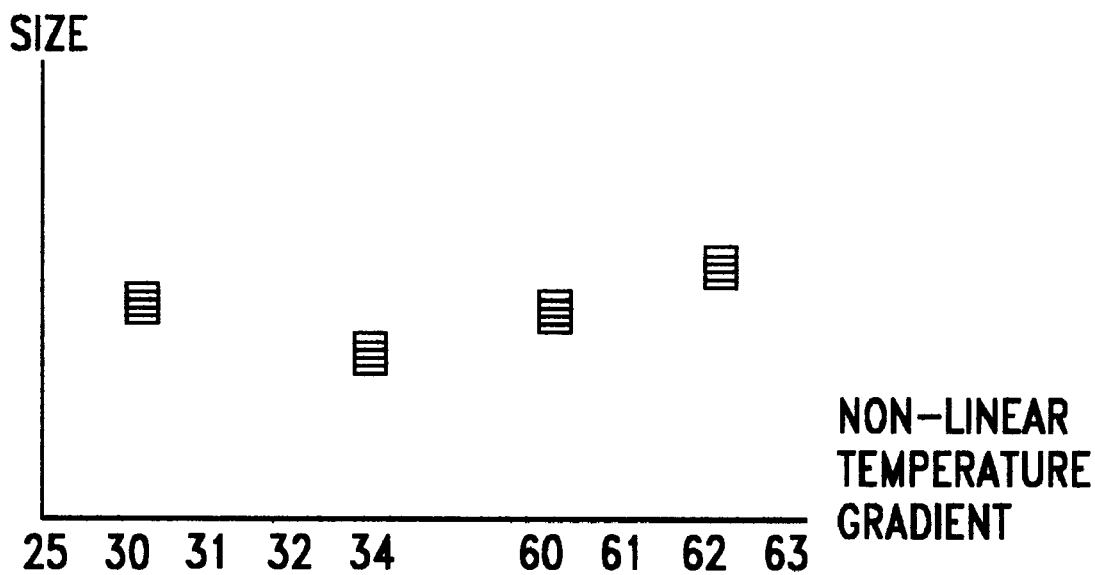
Figure 7:
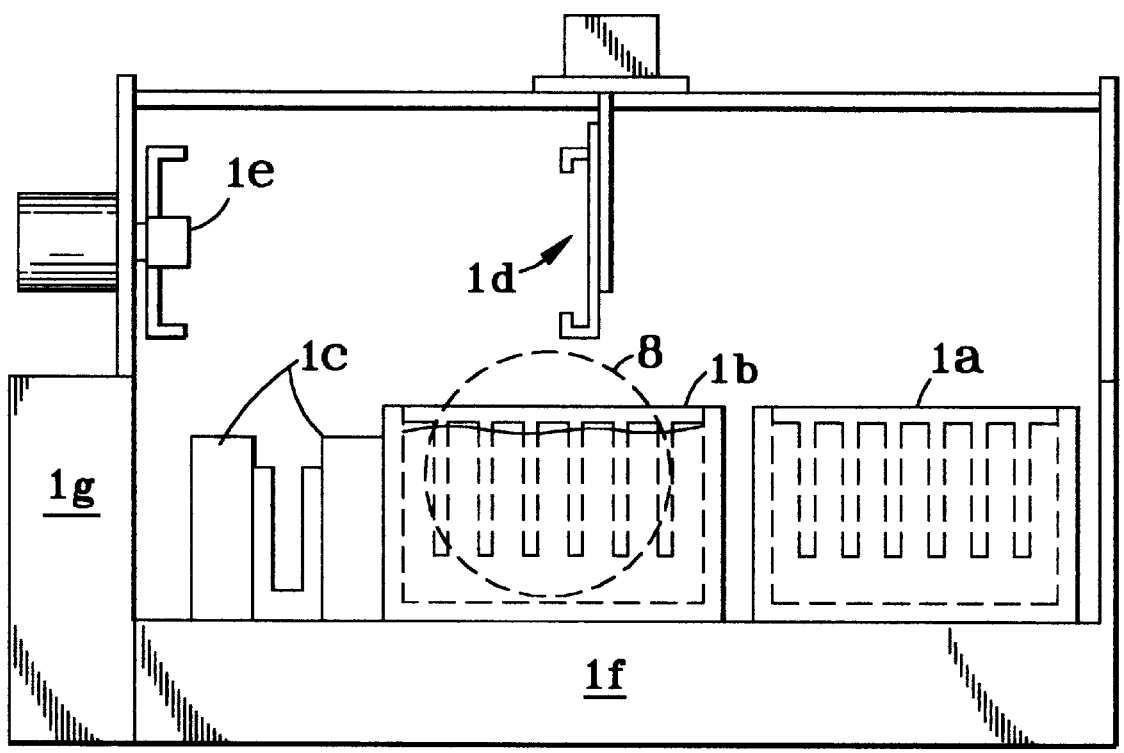
Figure 8:
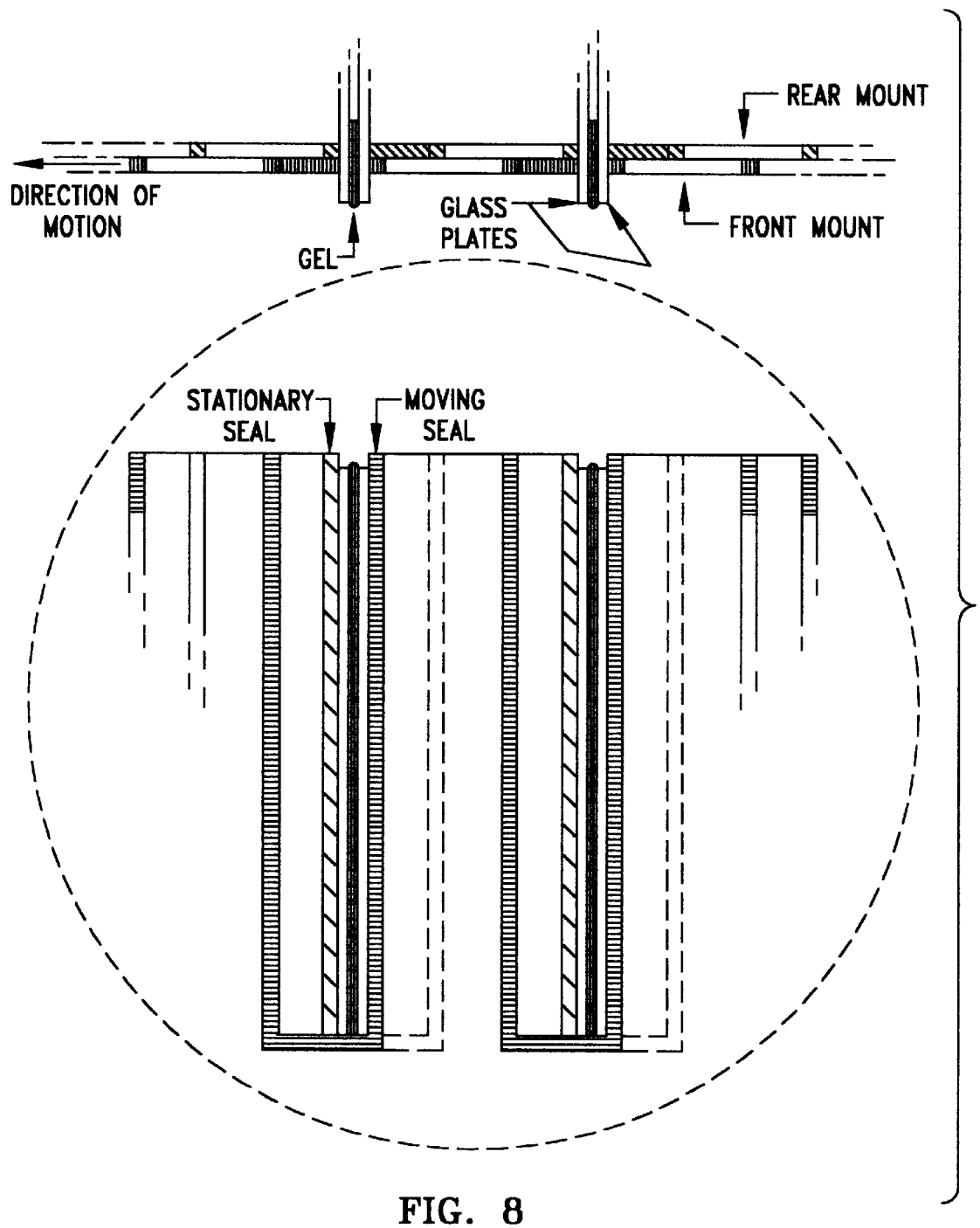
Figure 9:
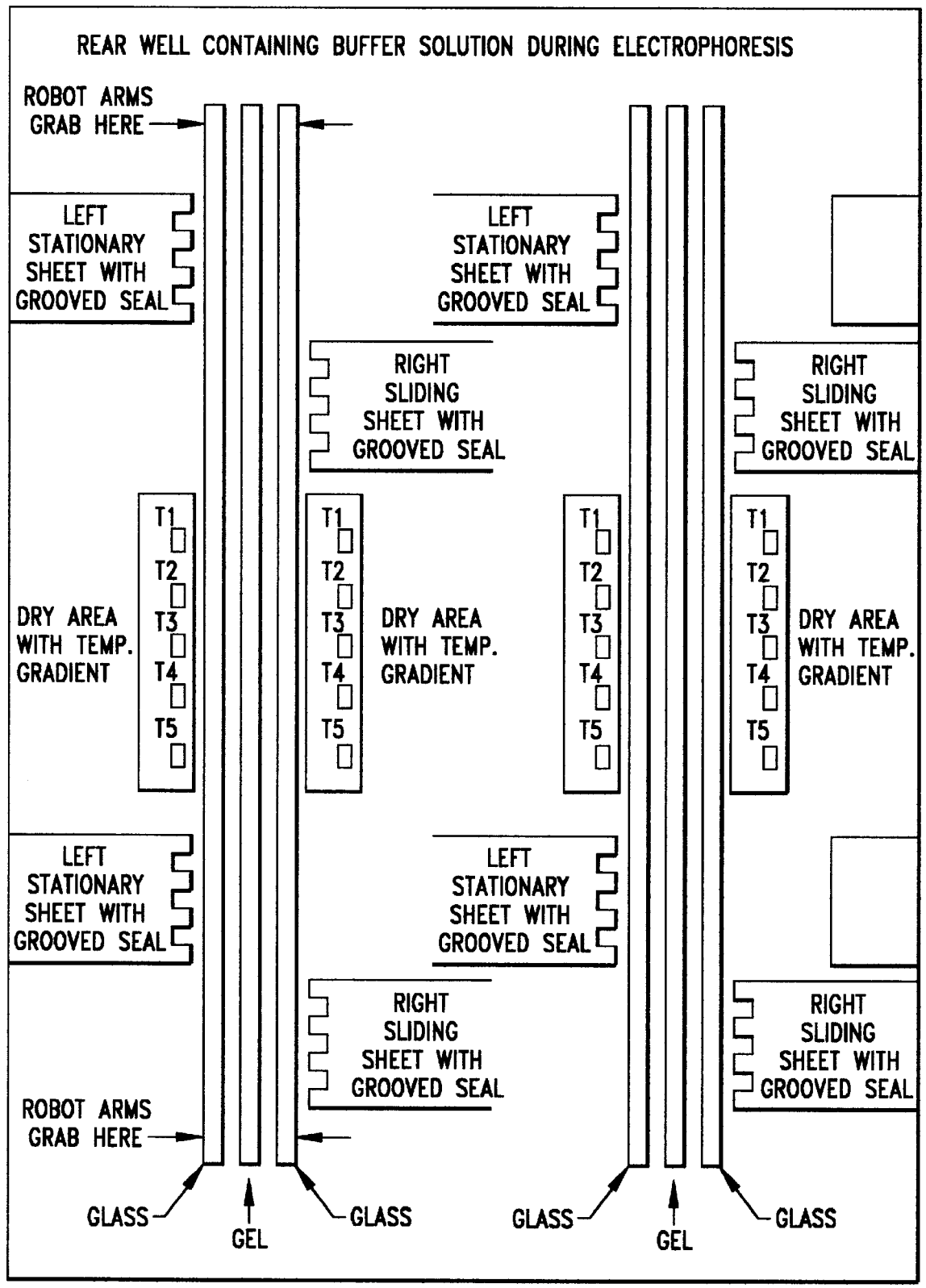
Figure 10:
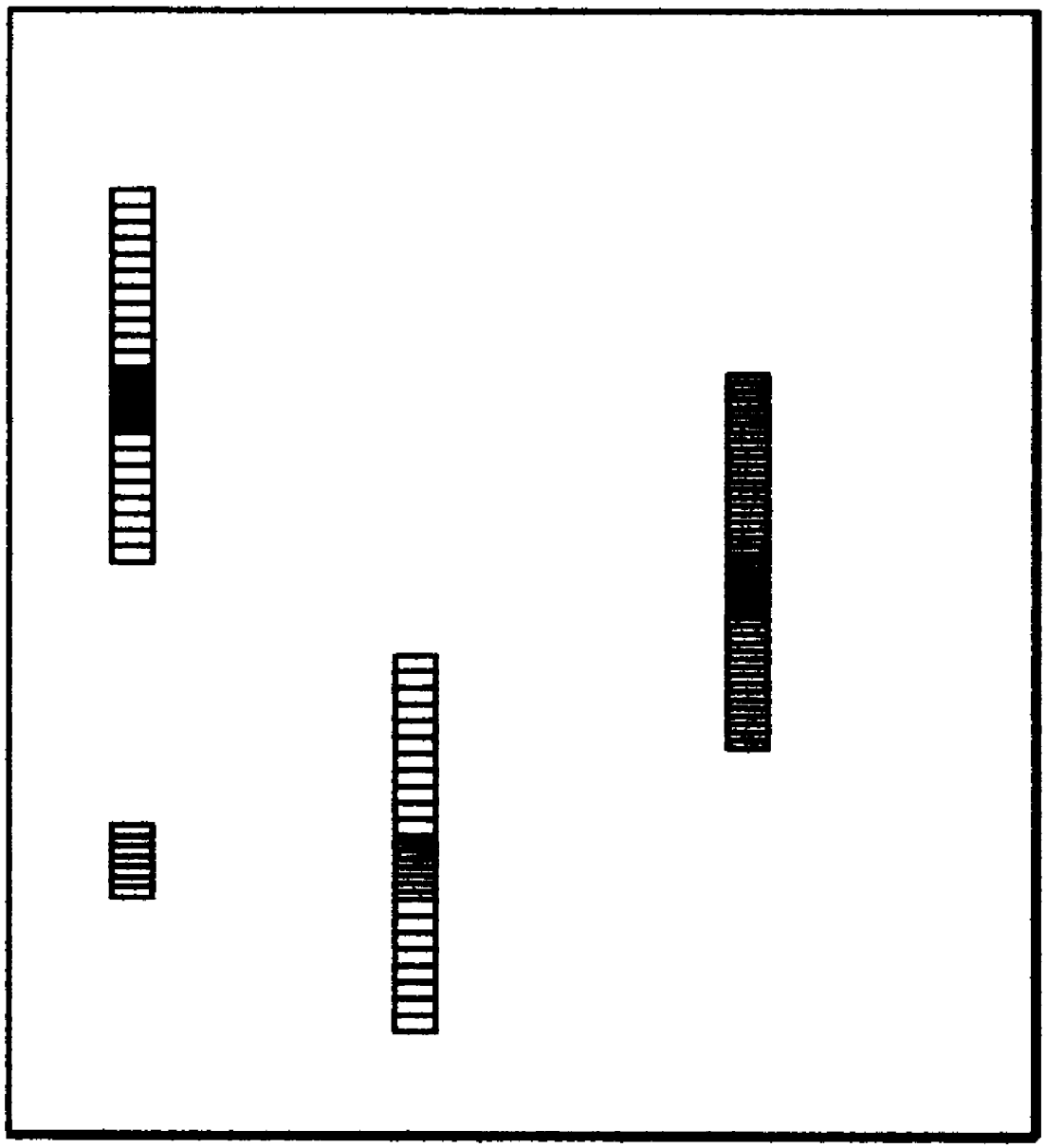

FIG. 6A and 6B compare the imaging results of linear and non-linear cell gradients, recommended by the present invention;

FIG. 7 is a side elevational view of the machine of FIG. 1;

FIG. 8 is an expanded view of the interlocking seating details in the electrophoresis modules of FIG. 7;

FIG. 9 is a top view of such module adapted for a two-gel system;

FIG. 10 illustrates smearing effects with multiple gene fragment cells.

Figure 11A:
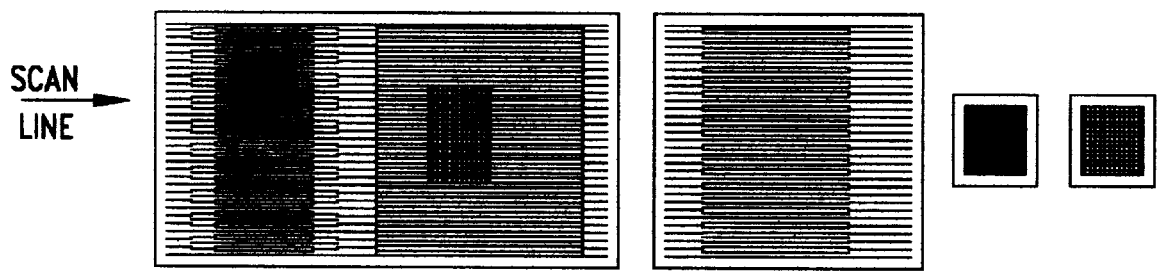
Figure 11B:
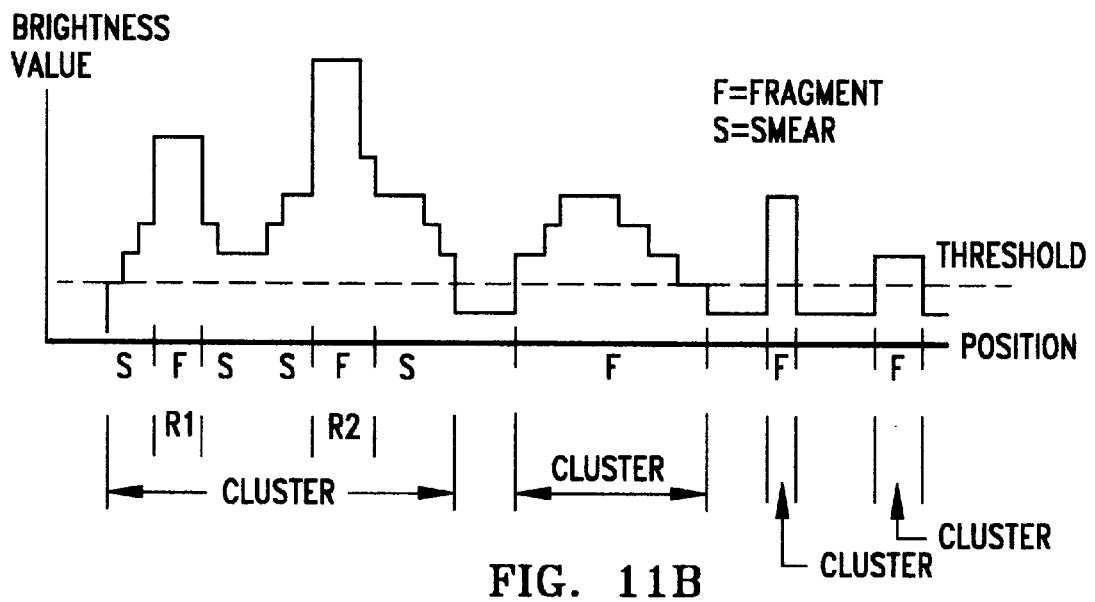
Figure 11C:
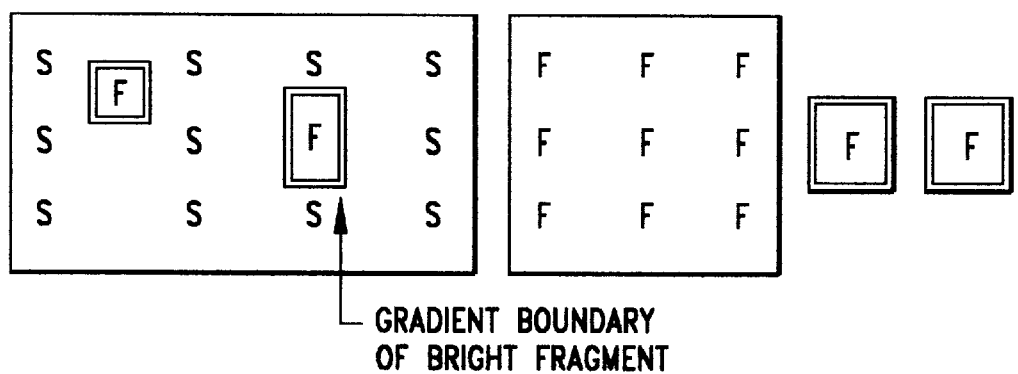
Figure 12:
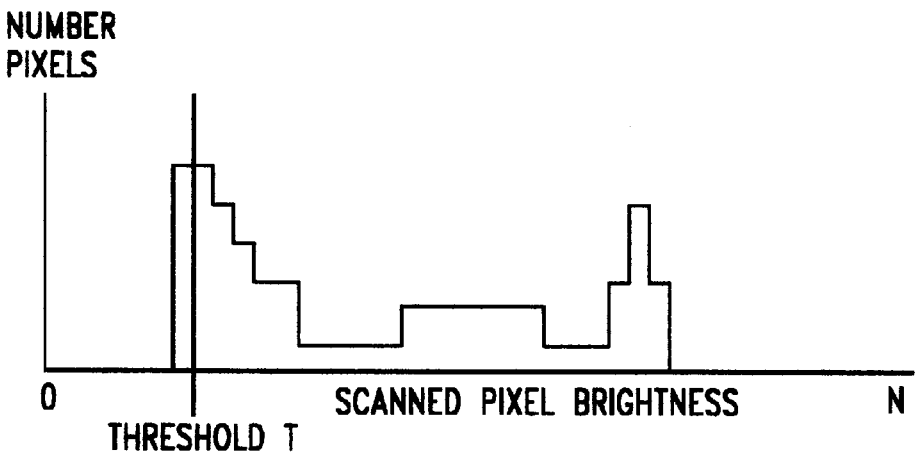
Figure 13:
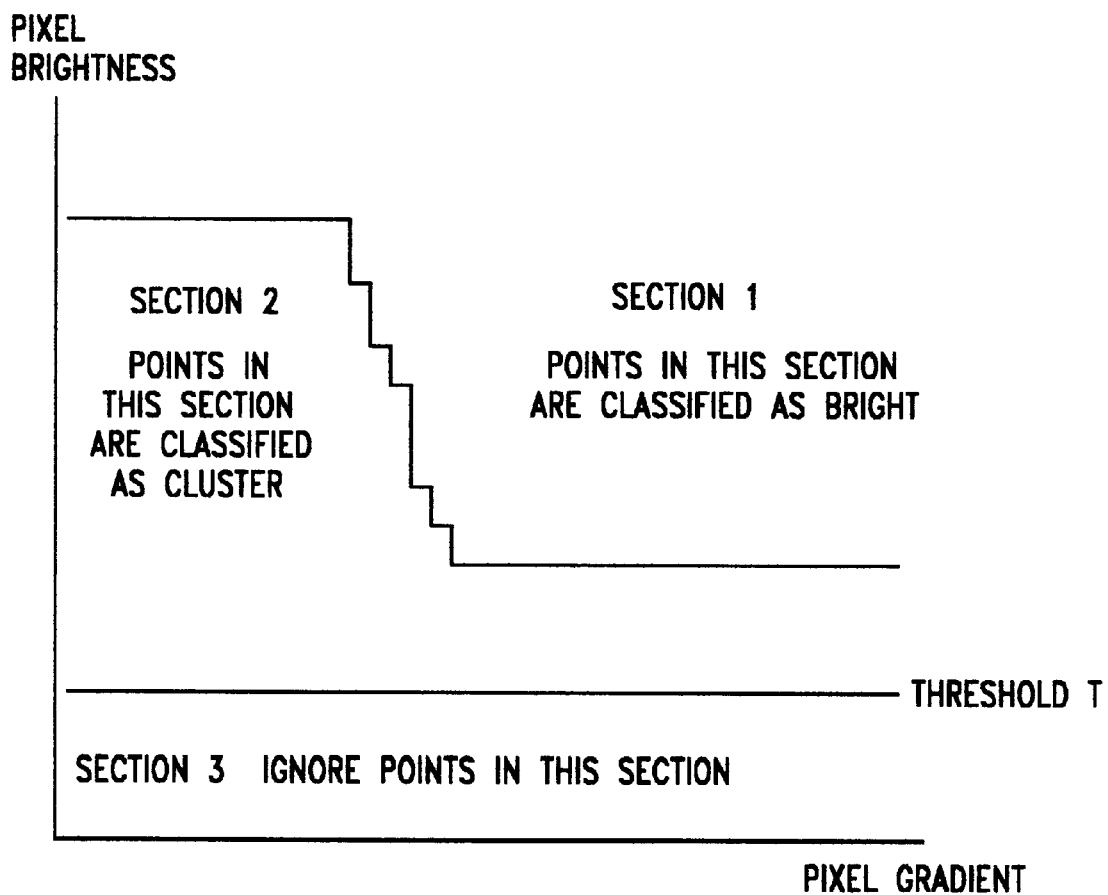

FIG. 11A, 11B, and 11C are respectively brightness displays, graphs and bright fragment boundary limits for fragment presentations as in FIG. 10; and FIGS. 12 and 13 are graphs, respectively, of pixels vs. scanned brightness of the gene fragment displays and of cluster, bright point and ignored regions of the image.

DESCRIPTION OF PREFERRED EMBODIMENT(S) OF INVENTION

Referring to the overall diagnostic machine system diagram of FIG. 1, the apparatus is shown containing the following component parts:

A. A robotically controlled 2-dimensional (2-D) electrophoresis apparatus, shown at 1b in FIG. 1, which can process single or multiple biological preparations, as later discussed; and incorporating a chemical gradient or programmable computer controlled temperature gradient. The temperature gradient can be programmed to provide a spatially linear or non-linear temperature profile to optimize detection of mutations as hereinafter explained;

B. An integrated robotically controlled scanner 1c for inspection of the fluorescently labeled electrophoresis patterns; and C. An intelligent algorithm for processing complex single or multi-color fluorescently labeled electrophoresis imagery which contains process variations and by-products.

These components, in accordance with the present invention, have been integrated in a novel manner with existing, though modified technologies to create a single system which performs the following operations:

Automated biological processing of gene DNA material to create a 2-dimensional image of DNA fragments from one or multiple genes.

Figure 2:
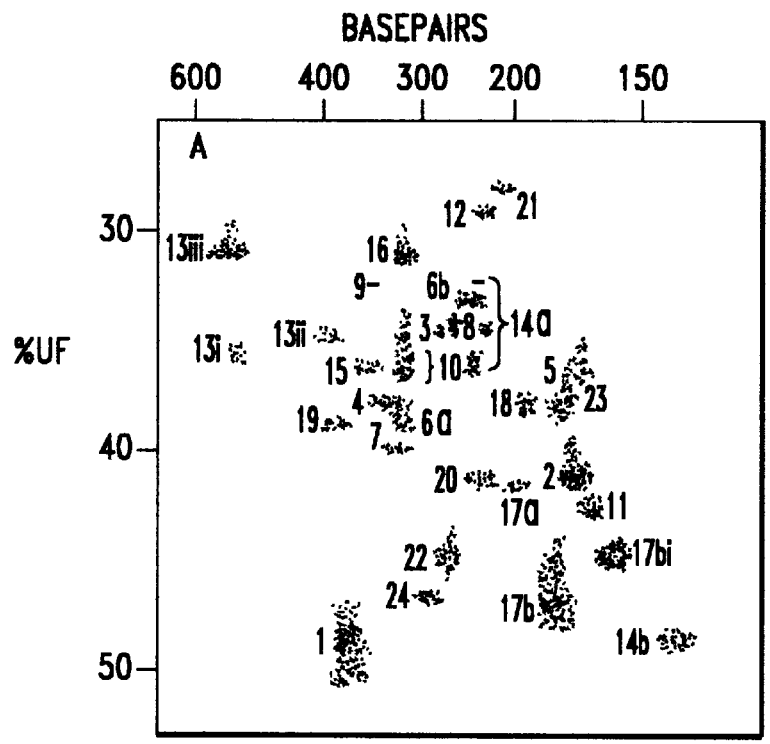
FIG. 2 is a copy of an actual image of electrophoretically separated gene fragments in the illustrative case of before-mentioned Cystic fibrosis (CF) gene.
Figure 3:
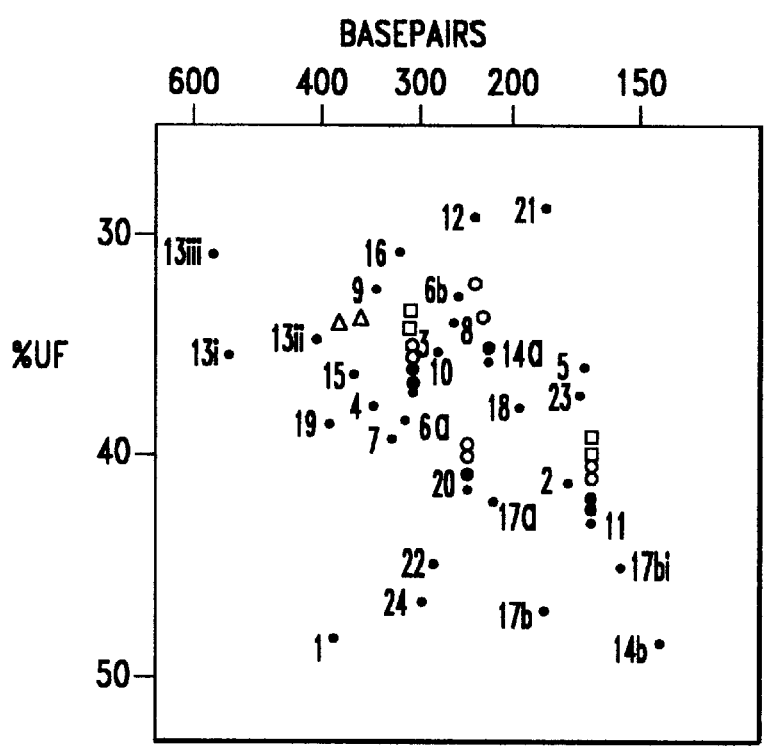
FIG. 3 is a standardized synthetic spot pattern indicating the positions of some of the mutations thus far detected.

FIG. 2, for example, is a 2-D electrophoretically displayed image of gene fragments from a mutated cystic fibrosis (CF) gene. FIG. 3 is a standardized synthetic spot pattern indicating the positions of some of the mutations thus far detected. The mutations can be observed as spatial shifts in the position of the fragments. Components A and B, listed above, are combined to produce the automated electrophoresis section of the instrument.

Automated image analysis to detect the precise position of DNA fragments from one or multiple genes.

Fragments appear as localized bright areas frequently surrounded by smeared by-products of the PCR biological preparation. The color of the fragments is a function of the fluro-label incorporated. Components B and C, listed above, are combined to automate the image analysis.

Loading Station

Operation consists of a lab technician inserting N fluorescently labeled biological preparations into a loading tray at 1a, FIG. 1. The preparations consist of gene or protein samples placed at one corner of different gels (for 2-D electrophoresis) or distributed along the top edge of the same gel (for 1-D electrophoresis). Gels are typically between 4 to 12 inches square) sandwiched between two optically transparent and electrically non-conductive plates, such as glass, as shown so-labeled in FIG. 4. The gels are prepared either with or without a chemical gradient of urea and formamide. The chemical gradient is not required but the machine can process gels with chemical gradients if desired.

The system, then, under automated robotic control, transports the N gels into the electrophoresis section of the apparatus (FIG. 1b). Theoretically, the system can be constructed to process a large number of gels in parallel. Since 2D electrophoresis requires one gel for each preparation, as the number of gels, N, increases, the length of the machine increases as 2×N because both the length of the loading tray and electrophoresis section increases. For practical purposes and size constraints, N is usually ≦30.

Robotically Controlled Two-Dimensional Electrophoresis Module With Computer Controlled Temperature Gradients To achieve the objective of a fully automated gene and/or protein analysis system, a modified electrophoresis module was found to be required that has the following new features and functions not present in any existing system:

1. Automatic robotic loading and unloading of multiple gel preparations, first from the loading tray 1a to the electrophoresis module 1b, and then after electrophoresis; to an automated inspection module 1c.
2. The fragile gels are kept between two glass plates at all times during handling, electrophoresis, and inspection to prevent damage to the gels. Fluorescent labels are attached to the fragments prior to the electrophoresis process so that the glass plates do not have to be separated to stain the DNA or protein fragments.
3. The electrophoresis module does not deposit any contaminants or optical artifacts onto the central regions of the glass plates, because there is no fluid or material in contact with the glass at any time. This ensures that artifacts do not interfere with interpretation of the spot patterns during the automated inspection process.
4. To optimize detection of mutations, the module provides the following types of computer-programmable, and computer-controlled temperature gradients; being adapted to provide any or all of spatially non-linear and temporally constant, spatially linear and temporally constant, spatially constant and temporally varying, or spatially constant and temporally constant environments. The importance and application for each of these types of gradients will be described later in this section.

To construct a system that has all of the above features, it was found not to be possible to use previously developed concepts such as the before-mentioned Ingeny electrophoresis machine.

Figure 4:
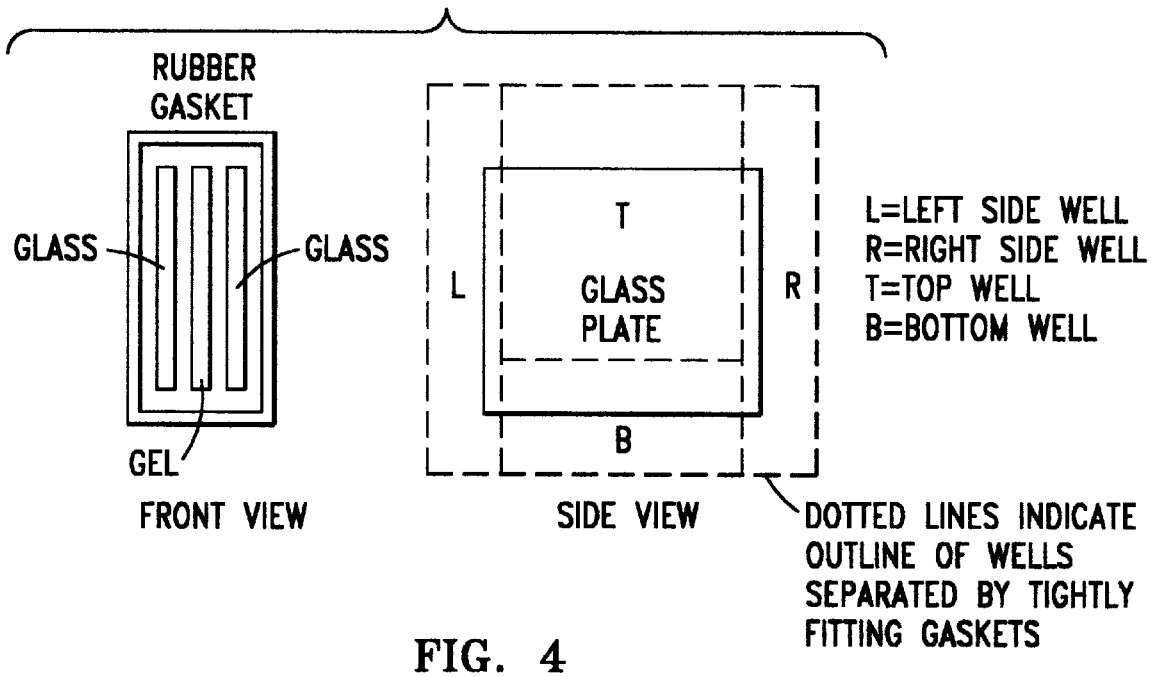
FIG. 4 shows front and side views of prior art gasketting requirements, illustrated for the previously described Ingeny electrophoresis system (ref. 15)
Figure 5:
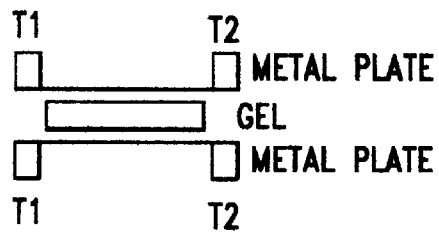
FIG. 5 shows a prior art linear temperature gradient one-dimensional electrophoresis cell.

To enable automatic gel loading and unloading, and to prevent buffer solution from contaminating the glass surface, it was found impractical to use manual gaskets installed along the edges of the plates, FIG. 4, such as wrapping a rubber band around the edge, since such prevents a robotic arm from gaining access to the plates for automatic handling.

In addition, it is disadvantageous to expose both glass plates to ionic buffer solution, which can leave a residue, when the top and bottom wells are required to be filled to perform the vertical electrophoresis in such prior machines. Such machines ,furthermore, cannot be modified to incorporate a spatially varying gradient because the temperature is stabilized by heating therein the ionic buffer solution to a fixed temperature and the solution encompasses all sides of the glass plates.

In accordance with the constructional departure of the invention to achieve its novel purposes, to the contrary, a series of N gels sandwiched between two glass plates and prepared with gene or protein samples to be processed is placed into the loading tray, placed into the loading bay of the instrument at 1a, FIG. 1.

A robotic arm 1d grabs each gel-plate combination and places it sequentially into the electrophoresis module 1b. The robot lifting device has two arms which are separated by slightly less than the width of the gel plates, such that the arms grab both plates containing the gels from horizontally opposite top and bottom edges so that no contact is made with the central region of the plates which is to be inspected later for mutations. The plates are raised vertically upwards, then moved horizontally to the correct position in the electrophoresis module, and then lowered into position. This operation is repeated until all the plates in the tray have been transferred into the electrophoresis module housing.

The electrophoresis module housing 1b is shown containing two wells, that span the front and rear sides of the module. The inner front and inner rear walls contain novel interlocks that open during loading to permit the robot arm to lower the glass plates into position.

FIG. 7 illustrates a front view of the system and FIG. 8 is a detailed view of the interlocks portion of FIG. 7. Each wall consists of two slotted sheets that slide together and apart like scissors. One sheet is stationary and the other sheet slides horizontally. Both sheets have seals along their vertical side and bottom edges. The sheets are separated while loading the gels. Once all the gel plates are loaded, the sheets slide together sealing against the surface of the plates, as shown in FIG. 8 and in the top view of FIG. 9. In FIG. 9 the wells and sliding sheets are shown for a two gel system. Electric pumps now automatically fill the front and rear wells with buffer solution from storage tanks located in the base of the module, as shown at 1f in FIGS. 1 and 7.

The system is now temperature stabilized using a computer programmable temperature gradient control system. One possible architecture of such is shown in FIG. 9 and operates as follows: In the center section between the two wells, a series of thermal conducting rectangular blocks T are placed close to, and parallel with, the glass plates labeled "glass". Each block T contains thermal heating rods and thermal measuring devices (thermistors, for example) inserted into the blocks and uniformly distributed along the length of each block. The rods are set to temperatures T1 through T5 via a computer that measures the temperature along the block using the thermal measuring devices, as is well known. This architecture enables the following types of gradients along the electrophoresis glass plate-gel units to be generated: spatially non-linear and temporally constant, spatially linear and temporally constant, spatially constant and temporally varying, or spatially constant and temporally constant. Once the desired thermal profile is achieved, electrophoresis begins. To initially separate fragments on the basis of size in the first dimension, a spatially and temporally constant temperature profile can be used.

Electrodes that span the entire length of the outer walls of the rear and front wells are automatically activated once the temperature has stabilized. The electrodes are connected to a high voltage power supply located within the instrument 1g (ref. 15) in FIG. 1. After a predetermined amount of time, all fragments will have stopped migration in the horizontal direction and this phase is assumed to be complete. Both wells are now drained, as the buffer solution is pumped back into the storage tanks located in the base of the instrument.

To perform the second orthogonal or vertical electrophoresis operation, which separates fragments using a predetermined temperature gradient, the wall interlocks slide open, and the robot arm 1d lifts, transports, and inserts the first gel plate combination into the rotation device 1e. The gel cell is then rotated 90°, placed back into the robot arm 1e, transported back to its correct slot position and lowered into the slot. This operation is repeated sequentially until all gels have been rotated. The interlocks are then closed and the wells are ready to be filled.

The wells are now refilled with buffer solution and the temperature profile is programmed to provide a gradient suitable for analyzing protein or DNA fragments as a function of base pair sequence. Once the temperature has stabilized, voltage is applied to the electrodes and the second electrophoresis step begins. For proteins, different kinds of polyacrylamide gels are used, and a temperature gradient is not required.

A particularly useful computer programmable temperature gradient profile in accordance with the invention, has a novel spatially non-linear temperature gradient, which greatly increases the detection of mutations. DNA fragments are migrated in vertical direction of increasing temperature gradient. At a specific temperature) the DNA strands separate as they melt. Consider the case, for example, where one wants to detect 4 different fragments that melt at: 30, 34, 60, and 62 degrees C., respectively, and are of approximately the same size, so they are not easily separated on the basis of size in the other or horizontal axis electrophoresis step. If a linear temperature gradient is applied FIG. 6a, ranging from 25 to 65 degrees, the fragments at 30 and 34 degrees will be clustered closely together at one end of the gel, and visually hard to separate, while the two fragments at 60 and 62 degrees will be even more tightly clustered at the other end and harder to visually separate, as evident in FIG. 6a. If a spatially non-linear gradient is used that rapidly reaches 30 degrees then slowly increases from 30 to 34 degrees over a few inches, then rapidly increases to 60 degrees over, say, an inch; and then slowly increases from 60 to 62 degrees, the fragments will be considerably more spatially separated and visually easier to detect, as shown in FIG. 6b. Combining this new form of computer controlled temperature gradient with the novel automation features of the invention totally eliminates the following labor intensive effort encumbering the prior art:

Creating gels with chemical gradients;

Manually loading and unloading samples into an electrophoresis apparatus;

Manually releasing each gel from between two glass plates so that they can be stained and placed into an imager; and Manually or semi-manually analyzing the gene fragment pattern looking for mobility shifts indicative of a mutation.

After the electrophoresis process has been completed the wells are drained, the interlocks are opened and each gel is sequentially transported, via the robot arm 1d, to the internal inspection station 1c, where it is scanned for mutations, as later more fully described.

It is now in order to examine the automated image analysis of the complex gene fragment patterns and the like.

Automated Image Analysis

Turning, first, to the appropriate algorithms for processing the DNA and/or protein fragments labeled with fluorescent markers so that they can be optically imaged and analyzed, the fluorescent markers are excited with one wavelength of illumination and emit light at a different longer wavelength. The illumination source is either a bulb or a laser. A filter is placed in the illumination path to permit only the excitation wavelength to excite the markers. Another optical filter is placed in the imaging path, before the detector, to block the excitation frequency and only pass the fluorescent emission wavelength. This ensures that when optically scanning the sample, the only source of energy that reaches the detector is fluorescent emission from the marked DNA fragments,for example.

When scanning the sample, fragments appear bright with varying intensities on a darker background. In an ideal case, fragment positions could be identified by detecting any particle brighter than the background. In practice, however, this simplistic approach does not work because many fragments are surrounded by process byproducts and artifacts that appear as elongated bright smears, surrounding the protein or DNA fragments, as more particularly described in earlier described FIG. 2. The area of these smears frequently overlap the position of a mutated fragment, making it very difficult to detect the mutation.

In protein disorders only a shift in spatial position indicates the mutation. In DNA disorders, however, three additional spots appear (ref. 15), but they are frequently within the area encompassed by the smear. To complicate the problem further, fragments significantly vary in intensity so that the intensity of a smeared region surrounding one fragment could be brighter than the intensity of a fragment at some other location in the gel.

FIG. 10 illustrates an example of four fragments, three of which are surrounded by smeared byproducts. For printing purposes, the fragments and smeared regions are indicated as black and gray shaded areas respectively. To better detect protein and DNA fragments in the presence of such process byproducts and artifacts, a new algorithm has been created in accordance with the invention and is used in combination with previously evolved and patented algorithms of the assignee of the present invention, Beltronics Inc., that discriminate edge transitions during optical scanning of differently reflective regions (ref. 13) and inspect geometric patterns to identify predetermined features and tolerances (ref. 14).

The newly invented algorithm of the invention and its integration in the system control of the invention is now explained with the aid of FIGS. 2 and 11A, 11B, and 11C. The latter show the brightness distribution for a scan line during image scanning that intersects numerous fragments, some of which are surrounded by smeared regions. The fragments are labeled F and the smeared regions S in FIGS. 11b and 11c. To isolate fragments in the presence of byproducts and artifacts the following conceptual operations are performed:

1. Isolate all pixels brighter than the background gel and group them into clusters as illustrated in FIG. 11A & 11B.
2. Identify all locally brighter regions contained within each cluster.
3. Measure the area of each local bright region to determine if it is within allowable size constraints using, for example, the before-mentioned Beltronics algorithm for measuring size and tolerance (ref 13). Regions within the cluster that satisfy the size constraints are classified as DNA gene fragments and the surrounding dimmer cluster is ignored.
4. If a cluster does not contain any fragments and is within cluster size constraints, it is classified as a fragment.

To compute cluster and locally bright region boundaries, the following computations are performed:

1. Create an intensity histogram over the entire gel consisting of N brightness levels as shown, for example, in FIG. 12.
2. Detect the darkest value in the histogram and create a threshold T slightly brighter than this value (typically 10–20% brighter)
3. All contiguous picture elements (pixels) brighter than threshold T are grouped into clusters as illustrated in FIG. 11B.
4. The absolute brightness value and two-dimensional slope or spatial brightness gradient of each pixel above threshold T is computed.

While the meaning of the absolute brightness value is self-explanatory, the gradient is a measure of how much brighter the point is relative to its neighborhood. It represents how much brighter a fragment boundary point is relative to its surrounding smeared region. If the combination of point brightness and gradient is sufficiently high, it is classified as a boundary point for a potential fragment.

FIG. 13 is a graph illustrating how a point would be so classified. Points lying in FIG. 13 section 1 are classified as bright. Points in section 2 are classified as cluster; and points in section 3 are ignored because they are below threshold T. The algorithm (ref. 14) uses a one-dimensional linear combination of gradients and brightness values to classify points. The present invention uses a two-dimensional gradient and a non-linear combination for classification.

Points classified as being bright will create a boundary ring that surrounds locally bright regions,as shown in FIG. 11C. The area contained within each boundary ring is computed. If the area is within a predeterimed range of acceptable values, the area is classified as a fragment. Area measurements can also be performed using the patented Beltronics algorithm described in reference 13.

5. Each cluster is examined to see if it contains any bright fragments; and if so, the area outside the fragments is classified as smear and is ignored.

6. The area of each cluster that does not contain any fragments is computed. If the cluster area lies within acceptable cluster size constraints, the cluster is classified as a fragment.

All remaining features that have not been classified as a fragment are considered to be artifacts or smeared regions and are ignored.

7. Once all the fragment locations have been identified and artifacts removed from the image, selected fragments in the gel are used as calibration points to compensate for dimensional variations of the entire pattern (spatial shifts, global stretching or shrinking). This is performed by mapping the selected points to those in a stored reference and performing a standard least squares fit on the data.

8. Once the dimensional variations are computed, the fragments are compared to the reference data set of fragments for the specific gene. Mismatches, especially at coordinates where mutated fragments are known to exist, should they be present, are automatically classified as mutations.

The algorithm stores and can provide the lab technician with the intensity of each mutated fragment, its spatial offset from its corresponding non-mutated position, and any other data of interest.

9. After each gel is inspected,it is returned to the loading tray by the robot arm, leaving all pertinent data in the computer.

This algorithm can either be implemented in hardware or software and on a variety of computers. One possibility is to use an AT compatible 486 or pentium computer produced by Compaq Computer Corporation. The scanner can be implemented using a laser such as a model 643-50YB dual frequency 488 nw & 568 nw unit produced by Omnichrome Corporation. The fluorescent detector can be implemented using a solid state detector model HUV-1100BG produced by EG&G corporation. The scanner mechanics is implemented using standard lead screws that move the laser beam synchronously with the detector in a raster scan X-Y coordinate system over the gel. The beam can either be swept using mirror scanners, such as those produced by General Scanning model GP-300, or the beam can be placed into a fiber optic bundle that is swept across the gel. The laser can also be replaced with a light bulb that has energy at the fluorescent excitation frequency.

The following is a table identifying the various references (ref. 1 through 15) cited during the above description of the invention.

Table of Earlier Cited References

1. Fischer, S. G. & Lerman, L. S. Cell 16,2693–2704, 1979
2. Lerman, L. S., Silverstein, K., Computational Simulation of DNA Melting and its Applications to Denaturing Gel Electrophoresis, Meth. Enzymol. 155, pg 482–501, 1987
3. Parallel Genome Analysis by Two-Dimensional DNA Typing, E. Mullaart, et al. Nature, Vol 365, Sep. 30, 1993
4. The D-Gene System , product literature by BIO-RAD, 1994
5. D. Riesner et al., Electrophoresis 10,377–389, 1989
6. Article, Nucleic Acids Research, Vol. 18, No. 9,
7. Article, Nucleic Acids Research, Vol. 21, No. 22,
8. The Fluorimager 575, product literature by Molecular Dynamics 1993
9. 373 DNA Sequencer, product literature by Applied Biosystems 1993
10. HPGE 1000 Electrophoresis System, product literature by Lab Intellligence, 1993
11. Laser-Excited Fluorescence Speeds DNA Sequencing, Laser Focus World, June 1994, p16–20
12. Ingenyvision reference pattern analysis
13. Beltronics patent "Method of and Apparatus for Geometric Pattern Inspection Employing Intelligent Image-Pattern Shrinking, Expanding and Processing to Identify Predetermined Features and Tolerances" U.S. Pat. No. 5,119,434, issued Jun. 2, 1992
14. Beltronics patent "Method of and Apparatus for Discriminating Sharp Edge Transitions Produced During Optical Scanning of Differently Reflective Regions" U.S. Pat. No. 4,697,088, issued Sep. 29, 1987
15. Automated Two-Dimensional DNA Typing, product literature by Ingeny B. V., Leiden, The Netherlands, 1992

The invention thus provides industry with the first fully automated gene and/or protein analysis system for volume clinical testing, embodying novel instrumentation and image processing algorithms created to implement the system.

Clearly, other types of scanners and reading methodologies ay be used in the automated system of the invention, provided that they achieve corresponding accurate reading results, and other shapes of electrophoresis cells and the like may also be employed.

Further modifications will also occur to those skilled in the art and such are considered to fall within the spirit and scope of the invention as defined in the appended claims.

What is claimed is:

1. An automatic system for analyzing protein and/or DNA gene fragment samples comprising in combination, an electrophoresis housing unit for receiving electrophoresis cells, each containing a protein or a gene fragment sample, and an optical scanning inspection unit, means for positioning optically transparent gel cells, each containing a protein or gene fragment sample, in the electrophoresis housing unit; computer-controlled means for thereupon applying voltage to electrodes extending transversely of the housing to effect electrophoretic migration of the protein or gene fragments along one dimension of the cell to separate the protein or gene fragments by size, and further comprising means operable following the electrophoretic migration along said one dimension for effecting electrophoretic migration of the protein or gene fragments along a second dimension of each cell that extends 90° to the said one dimension to separate the fragments in sequences, means for thereupon, under program control, sequentially presenting each cell image for optical scanning by said scanning inspection unit; means controlled by the computer program and operable during the scanning for identifying the desired fragments and their locations; and means for thereupon classifying the identified fragments.

2. The system claimed in claim 1, further comprising means for distinguishing the identified fragments from smear and other artifacts.

3. The system claimed in claim 2, further comprising means for comparing the identified fragments with reference locations of reference proteins and genes.

4. The system claimed in claim 3, further comprising means for returning the scanned cells to a storage location while storing all pertinent data related to the scanned fragments in the computer.

5. The system claimed in claim 1, further comprising means for setting up one of temperature or chemical gradients along the cells under the computer program control prior to the effecting of the electrophoretic migration along the second dimension.

6. A system as claimed in claim 5, wherein a temperature gradient is established and means is provided for adjusting the gradient to be non-linear along the cells.

7. A system as claimed in claim 1, further comprising means for setting up one of a temperature or chemical gradient along the cells under computer program control during one of the electrophoresis migrations.

8. An automatic system for analyzing protein and/or DNA gene fragment samples comprising in combination, an electrophoresis housing unit for receiving electrophoresis cells, each containing a protein or a gene fragment sample, and an optical scanning inspection unit; means for positioning optically transparent gel cells, each containing a protein or gene fragment sample, in the electrophoresis housing unit; computer-controlled means for thereupon applying voltage to electrodes extending transversely of the housing to effect electrophoretic migration of the protein or gene fragments of all the cells simultaneously, first along one dimension of the cells and then along a second dimension of the cells extending 90° to said one dimension; means for setting up one of a temperature or chemical gradient along the cells prior to effecting the electrophoretic migration along the second dimension, means operable under program control, for sequentially presenting each cell for image optical scanning to said scanning inspection unit; means controlled by the computer program and operable during the scanning for identifying the desired fragments and their locations, and means for thereupon classifying the identified fragments.

9. The system as claimed in claim 8 that is to analyze polymerase chain reaction base pair gene fragment samples contained in the cells, and wherein there is provided in the scanning inspection unit, under computer program control, means for identifying and contrasting the brighter gene fragments and their locations while distinguishing the same from smears and other artifacts; and means is further provided for automatically classifying the identified fragments and comparing the same with reference locations and spatial offsets of normal and mutated genes.

10. The system of claim 9 wherein the identifying and classifying is effected by means for:

a) setting a threshold of gene fragment image brightness for rejection;

b) grouping all continuous pixel elements brighter than said threshold into clusters;

c) computing the absolute brightness value and spatial brightness gradient of each pixel of brightness above the threshold;

d) classifying those combinations of point brightness and gradient that are sufficiently high, as boundary points for potential identifiable gene fragments;

e) computing the area within such boundaries and classifying as an identified fragment those within a predetermined range;

f) examining each cluster for possible containing of bright fragments and classifying areas outside such fragments as smears and for ignoring;

g) computing the area of clusters not containing bright fragments, and if within acceptable size constraints, classifying such as a fragment; and h) ignoring all remaining unclassified features as artifacts or smeared regions.

11. The system as claimed in claim 8 further comprising means for setting up a temperature gradient non-linearly across the cells.

12. The system claimed in claim 9 and in which there are provided basepair-sequenced gene fragments and such are fluorescent-labeled.

* * * * *